US006759057B1

(12) United States Patent
Weiner et al.

(10) Patent No.: US 6,759,057 B1
(45) Date of Patent: Jul. 6, 2004

(54) METHODS AND COMPOSITIONS USING LIPOSOME-ENCAPSULATED NON-STEROIDAL ANTI-INFLAMMATORY DRUGS

(75) Inventors: Alan L. Weiner, Lawrenceville, NJ (US); Pieter R. Cullis, Vancouver (CA)

(73) Assignees: The Liposome Company, Inc., Princeton, NJ (US); The University of British Columbia, British Columbia ( * ) Notice: Subject to any disclaimer, the term of this patent is extended or adjusted under 35 U.S.C. 154(b) by 1826 days.

(21) Appl. No.: 07/323,182

(22) Filed: Mar. 13, 1989

Related U.S. Application Data

(63) Continuation of application No. 06/873,584, filed on Jun. 12, 1986, now abandoned.

(51) Int. Cl.[7] .......................... A61K 9/127; B01J 13/02
(52) U.S. Cl. ....................... 424/450; 424/812; 264/4.1
(58) Field of Search ................ 424/450, 812; 264/4.6, 4.3, 4.1; 428/402.2

(56) References Cited

U.S. PATENT DOCUMENTS

| | | | |
|---|---|---|---|
| 3,395,223 A | 7/1968 | Berger | 424/195 |
| 3,993,754 A | 11/1976 | Rahman et al. | 514/12 |
| 4,029,773 A | 6/1977 | Beigler et al. | 514/53 |
| 4,145,410 A | 3/1979 | Sears | 424/450 |
| 4,224,179 A | 9/1980 | Schneider | 8/526 |
| 4,235,871 A | 11/1980 | Papahadjopoulos et al. | 424/89 |
| 4,377,567 A | 3/1983 | Geho | 424/1.1 |
| 4,378,354 A | 3/1983 | Ghyczy et al. | 424/199 |
| 4,427,649 A | 1/1984 | Dingle et al. | 424/450 |
| 4,522,803 A | 6/1985 | Lenk et al. | 428/402.2 |
| 4,528,193 A | 7/1985 | Ghyczy et al. | 514/78 |
| 4,588,578 A | 5/1986 | Fountain et al. | 428/402.2 |
| 4,687,661 A * | 8/1987 | Kikuchi et al. | 424/38 |
| 4,721,612 A | 1/1988 | Janoff et al. | 424/1.1 |
| 4,816,247 A * | 3/1989 | Desai et al. | 424/80 |
| 4,861,580 A | 8/1989 | Janoff et al. | 424/1.1 |

FOREIGN PATENT DOCUMENTS

| | | |
|---|---|---|
| EP | 92121 | 10/1983 |
| EP | 150732 | 8/1985 |
| JP | 58-179114 | of 1982 |
| WO | WO84/02076 | 6/1984 |
| WO | WO86/00238 | 1/1986 |

OTHER PUBLICATIONS

Chem Abst. 98:4011e, vol. 98, (1983).*
Boggs et al., 1984, J. Neurol. Sci. 66: 339–348.*
Myhdre, 1968, Can. J. Chem., 46:3071–77.*
Rouser, et al., 1967, Lipid Chromatographic Analysis, Inc., 1:99–162.*
Bangham, et al., Diffusion of Univalent Ions Across the Lamellae of Swollen Phospholipids. 1965, J. Mol. Biol., 13:238–252.
Papahadjopoulos, et al., Phospholipid Model Membranes I. Structural Characteristics of Hydrated Liquid Crystals, 1967, Biochim. Biophys. Acta., 135:624–638.
Dial et al., A Role for Milk Phospholipids in Protection Against Gastric Acid, 1984, Gastroenterol., 87:379–385.
Clemencon, et al., The Role of Bile Salts in Cysteamine–Induced Duodenal Ulcer in the Rat and the Ulceroprotective Property of Lysolecithin, 1984, Scand. J. Gastroenterol. Suppl. 19:116–120.
Moursi, et al., Effect of Melia Azedarach fruits on Gipsing–Restraint Stress–Induced Ulcers in Rats, 1984 Jpn. J. Pharmacol. 36:527–533.
Rainsford, et al., Gastroprotective and Anti–inflammatory Properties of Green Lipped Mussel (Perna canaliculus) Preparation, 1980, Arzneim. Forsch. 30:2128–2132.
Martin, et al., Membrane Damage by Bile Salts:The Protective Function of Phospholipids, 1981, J. Pharm. Pharmacol. 31:754–759.
Lichtenberger, et al., Role of Surface–Active Phospholipids in Gastric Cytoprotection, 1983, Science, 219:1327–1328.
Robert, et al., Effect of Prostaglandin $E_1$ on Gastric Secretion and Ulcer Formation in the Rat, 1979 Gastroenterol, 55:481.
Robert, et al., Cytoprotection by Prostaglandins in Rats, 1968, Gastroenterol, 77:433.
Quinn, et al., Plant Lipids and Their Role in Membrane Function, 1978, Prog. Biophys. Mol. Biol., 34:109–173.
Sprague, et al., Reconstitution of Light–Harvesting Complexes and Photosystem II Cores into Galactolipid and Phospholipid Liposomes, 1985, J. Cell Biol. 100:552–557.
Mörschel et al., Reconstitution of Cytochrome $f/b_6$ and $CF_o$–$CF_1$ ATP Synthetase Complexes into Phospholipid and Galactolipid Liposomes 1983, J. Cell Biol., 97:301–310.
Alving, et al., Comparative Properties of Four Galactosyl Lipids as Antigens in Liposomes, 1974, Immunochem., 11:475–481.
Wazna, et al., The Effect of Intestinal Fat on Histamine–Stimulated Gastric Secretion, 1977, J. Surg. Res., 23:415–421.
Murphy, D., The Importance of Non–Planar Bilayer Regions in Photo–synthetic Membranes and Their Stabilisation by Galactolipids, 1982, FEBS Lett. 150(1):19–26.
Shipley, et al., The Phase Behavior of Monogalactosyl, Digalactosyl, and Sulphoquinovosyl Diglycerides,, 1973, Biochem. Biophys. Acta., 311:531–544.

(List continued on next page.)

Primary Examiner—Andrew Wang
Assistant Examiner—My Chau T Tran
(74) Attorney, Agent, or Firm—Burns, Doane, Swecker & Mathis, L.L.P.

(57) ABSTRACT

Methods and compositions are described for the treatment of inflammatory diseases including the use of liposomes to deliver non-steroidal anti-inflammatory drugs. Drugs may be encapsulated in the liposomes during their preparation, or alternatively, are combined with the liposomes following their formation. The composition may include glycolipids such as galactolipids including digalactosyl diglyceride, and the liposomes may be made by a number of procedures. The compositions may be administered to mammals including humans.

16 Claims, No Drawings

OTHER PUBLICATIONS 310,495, Cullis et al., filed Feb. 13, 1989, Pending.
788,017, Cullis et al., filed Oct. 16, 1985, Abandoned.
622,690, Cullis et al., filed Jun. 20, 1984, Abandoned.
004,762, Cullis et al., filed Jan. 07, 1987, Pending.
622,502, Cullis et al., filed Jun. 20, 1984, Abandoned.
U.S. patent application Ser. No. 360,964, Janoff, et al., filed Jun. 26, 1989, pending.
U.S. patent application Ser. No. 284,751, Bally et al., filed Dec. 12, 1988, pending.
U.S. patent application Ser. No. 759,419, Janoff et al., filed Jul. 26, 1985, pending.
U.S. patent application Ser. No. 749,161, Bally et al., filed Jun. 26, 1985, abandoned.
U.S. patent application Ser. No. 638,809, Janoff et al., filed Aug. 08, 1984, abandoned.
U.S. patent application Ser. No. 122,613, Bally et al., filed Nov. 17, 1987, pending.
U.S. patent application Ser. No. 800,545, Cullis et al., filed Nov. 21, 1985, abandoned.
U.S. patent application Ser. No. 752,423, Bally et al., filed Jul. 05, 1985, abandoned.
U.S. patent application Ser. No. 773,429, Janoff et al., filed Sep. 10, 1985, pending.
U.S. patent application Ser. No. 280,551, Janoff et al., filed Dec. 06, 1998, pending.
U.S. patent application Ser. No. 786,740, Janoff et al., filed Oct. 15, 1985, abandoned.
Green Cross Corp., "Formulations of acetylsalicylate entrapped by lipids"1983; Chemical Abstracts, 98:40611e.
Mizushima, et al. "Antiinflammatory effects of indomethacin ester incorporated in a lipid microsphere", 1983; Chemical Abstracts, No. 99:93646x.

U.S. Patent Application Ser. No. 310,495, Cullis, et al., filed Feb. 13, 1989, pending.
U.S. Patent Application Ser. No. 788,017, Cullis, et al., filed Oct. 16, 1985.
U.S. Patent Application Ser. No. 622,690, Cullis, et al., filed Jun. 20, 1984.
U.S. Patent Application Ser. No. 004,762, Cullis, et al., filed Jan. 7, 1987, pending.
U.S. Patent Application Ser. No. 622,502, Cullis, et al., filed Jun. 20, 1984.
U.S. Patent Application Ser. No. 360,964, Janoff, et al., filed Jun. 26, 1989, pending.
U.S. Patent Application Ser. No. 284,751, Bally, et al., filed Dec. 12, 1988, pending.
U.S. Patent Application Ser. No. 759,419, Janoff, et al., filed Jul. 26, 1985, pending.
U.S. Patent Application Ser. No. 749,161, Bally, et al., filed Jun. 26, 1985.
U.S. Patent Application Ser. No. 638,809, Janoff, et al., filed Aug. 8, 1984, pending.
U.S. Patent Application Ser. No. 122,613, Bally, et al., filed Nov. 17, 1987, pending.
U.S. Patent Application Ser. No. 800,545, Cullis et al. filed Nov. 21, 1985.
U.S. Patent Application Ser. No. 752,423, Bally, et al., filed Jul. 5, 1985.
U.S. Patent Application Ser. No. 773,429, Janoff, et al., Sep. 10, 1985, pending.
U.S. Patent Application Ser. No. 280,551, Janoff, et al., filed Dec. 6, 1988, pending.
U.S. Patent Application Ser. No. 786,740, Janoff, et al., filed Oct. 15, 1985.

* cited by examiner

METHODS AND COMPOSITIONS USING LIPOSOME-ENCAPSULATED NON-STEROIDAL ANTI-INFLAMMATORY DRUGS

This application is a continuation of Ser. No. 06/873,584 filed Jun. 12, 1986 now abandoned.

BACKGROUND OF THE INVENTION

The present invention is directed to the treatment of disease states, such as inflammation, pain and fever, using compositions comprising a non-steroidal anti-inflammatory drug which may be encapsulated in a liposome. More particularly, the invention describes methods for reducing toxic side effects related to non-steroidal anti-inflammatory drugs by administering these drugs in liposomes, wherein the composition also includes a glycolipid.

A number of non-steroidal anti-inflammatory drugs ("NSAIDs") for the effective treatment of inflammatory illnesses, for example, rheumatoid arthritis, have been known. Examples of such drugs include salicylic acid acetate, indomethacin, and piroxicam. Since the inflammations for which one would be using such substances are chronic, the treatment will usually extend over a long period of time. Gastrointestinal irritation, including bleeding and ulcers, is a side effect commonly associated with NSAIDs. The present combination of an NSAID with a liposome permits efficacy of anti-inflammatory therapy of that of free drug alone, while preventing or ameliorating the gastrointestinal irritation or ulcers.

Liposomes are completely closed bilayer membranes containing an entrapped aqueous volume. Liposomes may be unilamellar vesicles (possessing a single membrane bilayer) or multilamellar vesicles (onion-like structures characterized by multiple membrane bilayers, each separated from the next by an aqueous layer). The structure of the resulting membrane bilayer is such that the hydrophobic (non-polar) "tails" of the lipid orient toward the center of the bilayer while the hydrophilic (polar) "heads" orient towards the aqueous phase.

The original liposome preparation of Bangham et. al. (*J. Mol. Biol.*, 13, 238–252 1965) involves suspending phospholipids in an organic solvent which is then evaporated to dryness leaving a phospholipid film on the reaction vessel. Then an appropriate amount of aqueous phase is added, the mixture is allowed to "swell", and the resulting liposomes which consist of multilamellar vesicles (MLVs) are dispersed by mechanical means. This technique provides the basis for the development of the small sonicated unilamellar vesicles described by Papahadjopoulos et al. (*Biochim. Biophys. Acta.* 135, 624–638 1967), and large unilamellar vesicles.

Other techniques that are used to prepare vesicles include those that form reverse-phase evaporation vesicles (REV), Papahadjopoulos et al., U.S. Pat. No. 4,235,871, stable plurilamellar vesicles (SPLV), Lenk et al., U.S. Pat. No. 4,522,803 incorporated herein by reference, monophasic vesicles (MPV), Fountain et al., U.S. Pat. No. 4,588,578 and incorporated herein by reference, freeze and thaw multilamellar vesicles (FATMLV), Bally et al., U.S. application Ser. No. 752,423, filed Jul. 5, 1985, and U.S. patent application Ser. No. 800,545, filed Nov. 21, 1985, both of which are incorporated herein by reference.

In a liposome-drug delivery system, the medicament is entrapped in the liposome and then administered to the patient to be treated. For example, see Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179, Lenk, et al., U.S. Pat. No. 4,522,803, and Fountain, et al., U.S. Pat. No. 4,588,578.

References citing the use of phospholipids to treat gastrointestinal ulceration have appeared in the literature; this effect due to the purported ability of the lipid to restore the stomach's natural protective barrier to irritants. For example, Dial et al., *Gastroenterology*, 87, 379–385 (1984), suggested the anti-ulcer activity of bovine milk was due to its concentration of dipalmitoyl phosphatidylcholine. Other studies cite lysolecithin (Clemencon et al., *Scad. J. Gastroenterol.* Suppl., 19, 116–120, 1984) and lipids isolated from both the fruits of the *Melia azedarach* plant, and the mussel *Perna canaliculus* (Al-Khatib, *Jpn. J. Pharmacol.*, 36, 527–533, 1984, and Rainsford et al., *Arzneim.-Forsch.*, 30, 2128–2132, 1980, respectively), as ulceroprotective agents in rats.

Another study assessing membrane damage incurred by sodium dodecyl sulfate cites phosphatidylcholine (Martin et al., *J. Pharm. Pharmacol.*, 33, 754–759, 1981) as a protective agent against such damage. Finally, Lichtenberger et al. (*Science*, 219, 1327–1328, 1983) studied the ameliorative effects of a liposomal phospholipid suspension composed of 135 ug of dipalmitoyl phosphatidylcholine, and 15 ug each of phosphatidylethanolamine, phosphatidylglycerol, phosphatidylinositol, and sphingomyelin. They postulate the enhanced protection due to formation of an absorbed hydrophobic layer between the gastric epithelium and the luminal contents. Prostaglandins have been cited as protectants against gastric ulcerogenesis and bleeding in laboratory animals and man (Robert et al., *Gastroenterology*, 77, 433, 1979, and Robert et al., *Gastroenterology*, 55, 481, 1968), however Lichtenberger et al. (vide infra) determined that prostaglandin synthesis was not required for extrinsic phospholipid-induced gastric protection. However, when rats were dosed with Prostaglandin $E_2$, rat stomach mucosa demonstrated a 2–6 fold increase in the major gastric surface protective surfactant with the greatest enhancements seen in concentrations of phosphatidylethanolamine and phosphatidylcholine.

In addition, Lichtenberger et al. European Pat. Appl. 92121, published Oct. 26, 1983, suggest phospholipid compositions for the treatment of ulcer. An application for similar compositions combined with a prostaglandin, for treatment of gastric and intestinal ulcers is Imagawa et al., European Pat. Appl. 150732, published Aug. 7, 1985. A further reference suggesting anti-ulcer compositions is Amen et al., U.S. Pat. No. 4,029,773, for a saccharose, amino acid and trigylceride mixture.

Ghyczy et al., U.S. Pat. No. 4,528,193, discloses compositions and methods of treating inflammation comprising phospholipids and non-steroidal anti-inflammatory drugs where the molar ratio is about 1:0.1 to 1:20. The mixture is prepared by co-solubilizing the drug and lipid in organic solvent, followed by removal of the solvent by distillation. Alternatively, the components are co-mixed in water. The solutions so obtained are then lyophilized.

A major plant galactolipid, digalactosyl diglyceride (DGDG) has been used to prepare liposomes. DGDG accounts for about 40% of the total lipid content of higher plant chloroplast and thylakoid membranes (Quinn et al., *Prog. Biophys. Molec. Biol.*, 34, 109–173, 1978). It has been used in studies where photosystems utilizing chlorophylls and cytochromes are reconstituted into liposomes (Sprague et al.,*J. Cell Biol.*, 100, 552–557, 1985, and Morschel et al., *J. Cell Biol.* 97, 301–310, 1983, respectively). Studies involving immunological activity of DGDG in liposomes as measured by complement dependent glucose release (Alving et al., *Immunochemistry*, 11, 475–481, 1974) and the reactivity of sera from multiple sclerosis patients with DGDG liposomes and its ability to cause complement-mediated lysis of the liposomes (Boggs et al., *J. Neurol. Sci.*, 66, 339–348, 1984) have been performed. DGDG has been suggested as a minor liposome component for the purpose of delivering liposomal-encapsulated drugs to hepatocytes (Geho, U.S. Pat. No. 4,377,567).

There is an ongoing need for compositions which can buffer the unwanted gastrointestinal side effects of NSAIDs.

SUMMARY OF THE INVENTION

In view of the foregoing state of the art, it is an object of the present invention to provide compositions and methods of administration for non-steroidal anti-inflammatory drugs, which are less likely to produce ulcerogenic effects when used to treat chronic inflammatory diseases such as arthritis, or when used for their general analgesic and antipyretic effects.

Compositions are provided for non-steroidal anti-inflammatory drugs with a glycolipid. The glycolipid can be a glycosphingolipid or a galactolipid, such as digalactosyl diglyceride. The non-steroidal anti-inflammatory drugs can be any of the group including those such as aspirin, piroxicam, indomethacin, ibuprofen, naproxen and sulindac. The pharmaceutical composition may be a liposome composition composed of the above-mentioned glycolipids.

Methods for treating disease states such as inflammation, pain and fever with the pharmaceutical compositions are also given.

DETAILED DESCRIPTION OF THE INVENTION

The following abbreviations will be employed:

SPLV—stable plurilamellar vesicle
MLV—multilamellar vesicle
MGDG—monogalactosyl diglyceride
DGDG—digalactosyl diglyceride
CHS—cholesterol hemisuccinate
HSPC—hydrogenated soy phosphatidylcholine
THS—tocopherol hemisuccinate
MPV—monophasic vesicle
FATMLV—MLVs produced by a-freeze and thaw technique
VET—vesicles formed by one or more extrusions through filter apparatus
REV—reverse phase evaporation vesicle
NSAID—non-steroidal anti-inflammatory drug The non-steroidal anti-inflammatory drugs are a highly effective group of drugs, however, their use is limited due to their toxicity. We have found that administering NSAIDs encapsulated in liposomes reduces gastrointestinal side effects including ulceration while maintaining their efficacy.

Suitable lipids that may be used in the present invention include glycolipids such as glycosphingolipids and galactolipids such as digalactosyl diglyceride (DGDG) or monogalactosyl diglyceride (MGDG) and DGDG and/or MGDG in combination with phospholipids such as phosphatidylcholine, phosphatidylserine, phosphatidylinositol, or phosphatidylethanolamine and their derivatives and sterol or tocopherol monoesters of diacids, such as cholesterol hemisuccinate and tocopherol hemisuccinate, respectively.

The liposomes that may be used in the invention include, but are not limited to MLVs, small or large unilamellar vesicles (SUVs or LUVs, respectively), VETs and those having equal solute distribution, such as SPLVs, MPVs, and FATMLVs.

A variety of methods may be used to prepare a liposome composition comprising an NSAID and a galactolipid, such as DGDG. In one method, the NSAID is combined with the lipid in organic solvent, the solution rotary evaporated to a thin film and finally, the film hydrated with an aqueous medium such as aqueous buffer, forming liposomes. Such a procedure forms MLVs.

Another method for preparing NSAID-galactolipid liposomes is to combine the NSAID with the galactolipid in organic solvent, rotary evaporate the solution to a thin film, and dissolve the dried film in ethanol to which has been added an aliquot of an aqueous medium such as aqueous buffer. This solution is then rotary evaporated to a thin film, and the film then hydrated with aqueous medium, forming liposomes. Such a procedure forms MPVs.

Yet another method for preparing NSAID-galactolipid liposomes is to combine the NSAID with the galactolipid in organic solvent, rotary evaporate the solution to a thin film, and resuspend the film in diethyl ether. A small aliquot of an aqueous medium such as aqueous buffer is then added to the organic solvent solution, and this solution is dried under nitrogen gas to a paste while sonicating in a bath sonicator. The paste is then hydrated with an aqueous medium, forming liposomes. Such a procedure forms SPLVs.

A further method for preparing NSAID-galactolipid liposomes is to form MLVs as described above, then subject these MLVs to a number of freeze and thaw cycles. Such cycles are carried out by first rapidly cooling the MLV suspension to obtain a frozen lipid-aqueous medium mixture, and then warming the mixture. The freezing and warming steps are preferably performed at least about five times. Such vesicles have an equal solute distribution and are known as FATMLVs.

Yet another method for preparing NSAID-galactolipid liposomes is to form MLVs as described above and extrude these liposomes through a filter under pressues of about 700 psi. Such resulting vesicles are known as VETs.

SPLVs can be prepared according to the procedures of Lenk et al., U.S. Pat. No. 4,522,803, relevant portions of which are incorporated herein by reference. MPVs can be prepared according to the procedures of Fountain et al., U.S. Pat. No. 4,588,578, relevant portions of which are incorporated herein by reference. FATMLVs, vesicles formed by a repetitive freeze-and-thaw technique, can be prepared according to the procedures of Bally et al., U.S. patent application Ser. No. 800,545, filed Nov. 21, 1985, relevant portions of which are incorporated herein by reference. VETs, vesicles produced by extrusion at pressures up to about 700 psi through a filter, can be prepared according to the procedures of Cullis et al., U.S. patent application Ser. No. 788,017, filed Oct. 16, 1985, relevant portions of which are incorporated herein by reference.

Both CHS- and THS-containing vesicles may generally be prepared by any method known to the art for preparing vesicles. In particular, see the procedures of the copending patent applications of Janoff et al., U.S. patent application Ser. No. 721,630, entitled "Steroidal Liposomes", filed Apr. 10, 1985, Janoff et al., U.S. patent application Ser. No.,. 773,429 entitled "Steroidal Liposomes", filed Sep. 10, 1985, and Janoff et al., Ser. No. 786,740, entitled "Alpha- Tocopherol Based-Vesicles", filed Oct. 15, 1985, respectively, relevant portions of which are incorporated herein by reference. According to these procedures, the powdered forms of sterol or tocopherol monoesters of diacids, such as CHS or THS are added to an aliquot of aqueous buffer, and vortexed to fully suspend the dispersions forming MLVs. The dispersions are then sonicated in a water bath for several hours forming SUVs, and the drug powders added directly to these sonicated vesicles, and vortexed to fully disperse.

Glycolipids that may be used in forming the vesicles of the invention include glycosphingolipids and galactolipids such as monogalactosyl diglyceride (MGDG) or digalactosyl diglyceride (DGDG), preferably DGDG. DGDG occurs in nature as a plant lipid in chloroplasts and has the structure:

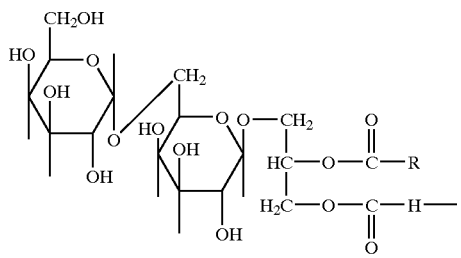

wherein each R substituent is in the $C_{15-C17}$ chain range, ca 20% palmitic, 9% oleic, 66% linoleic, the balance being stearic, linolenic, and other fatty acids. (Myhdre, *Can. J. Chem.*, 46, 3071–77, 1968)

The MGDG molecule has a single neutral galactose residue on its polar headgroup. Biophysical studies ($^{13}$C-longitudinal relaxation times) imply that the MGDG headgroup is significantly smaller than that of other lipids such as DGDG and phosphatidylglycerol. Hence, the molecule has a cone shaped structure, with the interactions of the highly unsaturated acyl chains giving it a relatively bulky hydrophobic region. Thus MGDG does not form lamellar structures but forms a hexagonal-II structure under hydration. Mixtures of MGDG with bilayer forming lipids will adopt a bilayer structure at concentrations of MGDG up to about 60 mol %. Higher proportions of MGDG will result in lipidic particles and other nonbilayer structures.

DGDG has an additional galactose unit on the polar headgroup compared to MGDG, thereby giving it a relatively bulky headgroup, but it also has bulky hydrophobic acyl chains. Structurally, DGDG forms cylindrical-shaped structures and induces bilayer organization in membranes. This feature makes DGDG the preferred galactolipid of the two for the formation of liposomes. In combined aqueous dispersions, MGDG and DGDG form mixed lamellar and inverted micelle phases at a 2:1 weight ratio. Studies have been undertaken to form liposomes with MGDG and DGDG combinations using detergent solubilization techniques with Triton X-100. Using this technique, bilayer structures may be formed using both galactolipids only up to a MGDG:DGDG weight ratio of 20:80. $Hex_{II}$ tubes formed in preparations using 30% or greater MGDG. Mixtures containing equal weights of MGDG and DGDG produce structures with only traces of bilayer areas containing lipidic particles.

Another technique for forming MGDG/DGDG liposomes is to solubilize both lipids below 20° C. in a fluorinated hydrocarbon (such as Freon-22) below the boiling point of the fluorinated hydrocarbon. An aqueous medium is then added forming an emulsion. The emulsion is then warmed above the boiling point of the fluorinated hydrocarbon (e.g. 20° C.), to remove the fluorinated hydrocarbon, resulting in liposome formation.

In combined dispersions of MGDG and DGDG used to form reverse phase evaporation vesicles (REVs), bilayers accommodate slightly greater amounts of MGDG before major surface irregularities appear, as compared to the detergent dialysis technique. Liposomes formed using a 40:60 weight ratio of MGDG:DGDG contain hex-II tubular arrays in bilayer vesicles. Clumping of the lipids in the aqueous phase does not occur until 70% MGDG is reached. Both MGDG and DGDG may be successfully combined with other lipids such as phospholipids, sterols such as cholesterol esters, or phenols such as tocopherols to form liposomes.

A liposome preparation can also be composed of a combination of CHS and THS, or other organic acid derivatives of a sterol and a tocopherol.

Where necessary, as in the SPLV and MPV procedures, organic solvents may be used to solubilize the lipid during vesicle preparation. Suitable organic solvents are those with a variety of polarities and dielectric properties, including chloroform, acetone, methylene chloride, diethyl and petroleum ethers, and mixtures of chloroform and methanol.

Liposomes entrap an aqueous medium which is enclosed by the lipid bilayers. The aqueous medium can be for example, water or water containing a dissolved salt or buffer. Examples of such salts or buffers can be sodium chloride and phosphate buffered saline (PBS). Other buffers include but are not limited to Tris-HCl (tris (hydroxymethyl)-aminomethane hydrochloride), and HEPES (N-2-hydroxyethyl piperazine-N'-2-ethane sulfonic acid). Buffers may be in the pH range of between about 5.0 and about 9.5. In the preferred embodiment, the preparations are hydrated with phosphate buffered saline (PBS) at pH of between about 5.0 and 9.5, preferably about pH 7.4. In the case of CHS- and THS-containing vesicles which employed the Tris salt forms of CHS and THS, a Tris/HCl buffer at pH of about 7.4 was used.

The entrapped bioactive agents used in the present invention are non-steroidal anti-inflammatory drugs (NSAIDs) including but not limited to: acemetacin, alclofenac, azapropazone, benoxaprofen, benrilate, carprofen, choline-magnesium trisalicylate, diclofenac, diflunisal, etodolac, fenbufen, fenclofenac, fenoprofen, fentiazac, feprazone, flufenamino acid, flurbiprofen, glucametacin, ibuprofen, indomethacin, indoprofen, isoxicam, ketoprofen, magnesium salicylic acid, meclofenamic acid, mefenamino acid, methylsalicylate, naproxen, niflumic acid, osmosin, oxaprozin, oxyphenbutazone, phenylbutazone, piroxicam, pirprofen, salicylamide, salicylic acid, salicylic acid acetate (aspirin), salicylsalicylic acid, sodium salicylate, sulindac, suprofen, tenoxicam, tiaprofenic acid, tolmetin, zomepirac, and the pharmaceutically acceptable salts thereof.

NSAIDs are generally lipophilic, and partition within the lipid portion of the liposome. They may be administered within lipid vesicles or, in admixture with a pharmaceutically-acceptable carrier selected with regard to the intended route of administration and standard pharmaceutical practice. The proportional ratio of active ingredient to carrier will naturally depend on the chemical nature, solubility, and stability of the active ingredient, as well as the dosage contemplated. For the oral mode of administration, an NSAID-liposome composition of this invention can be used in the form of tablets, capsules, lozenges, troches, powders, syrups, elixirs, aqueous solutions and suspensions, and the like. In the case of tablets, carriers which can be used include lactose, sodium citrate, and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, certain sweetening and/or flavoring agents can be added. For parenteral administration or injection via intravenous, intraperitoneal, intramuscular, subcutaneous, intra-aural or intra-mammary route sterile solutions of the NSAID-liposome composition are prepared and the pH of the solutions are suitably adjusted and buffered. For intravenous use, the total concentration of solutes should be controlled to render the preparation isotonic.

In another example of their use, vesicle-entrapped compounds may be incorporated into a broad range of topical dosage forms including but not limited to gels, oils, emulsions and the like. For instance, the suspension containing the entrapped compound may be added to the aqueous phase as an ingredient in any type of liposome preparation (eg., SPLVs, MPVs, FATMLVs, MLVs, SUVs, LUVS, REVs and others). This allows the entrapment of the water-insoluble compound in the phospholipid liposomes. Such preparations may be administered as topical creams, pastes, ointments, gels, lotions and the like for direct application to the inflamed area.

NSAIDs are generally administered to humans in dosages ranging from about 20 mg to about 3200 mg a day depending on the NSAID. For example, indomethacin dosage ranges from 50–200 mg/day. Ibuprofen dosage ranges from 1200–3200 mg/day. The actual dosages should generally be determined by a physician. Similarly, other mammals such as horses may be administered these compounds in dosage ranges of 2 mg/kg/day–800 mg/day (regardless of weight). For example, naproxen dosage for horses is 10 mg/kg/day in two divided dosages when given by oral route of administration. The prescribing physician or veterinarian will ultimately determine the appropriate dose for a given subject, and this can be expected to vary according to the age, weight and response of the individual subject, as well as the nature and severity of the subjects' symptoms.

The liposomes of the present invention may be dehydrated, thereby enabling storage for extended periods of time until use. Standard freeze-drying equipment or equivalent apparatus may be used to dehydrate the liposomes. Liposomes may also be dehydrated simply by placing them under reduced pressure. Alternatively, the liposomes and their surrounding medium can be frozen in liquid nitrogen prior to dehydration. Dehydration with prior freezing may include the presence of one or more protective sugars in the preparation, according to the process of Janoff et al., U.S. application Ser. No. 759,419, filed Jul. 26, 1985, entitled "Dehydrated Liposomes", relevant portions of which are incorporated herein by reference. Examples of protective sugars that may be used include but are not limited to trehalose, maltose, sucrose, glucose, lactose and dextran. Alternatively, multilamellar vesicles may be dehydrated with prior freezing without protective sugars. When the dehydrated liposomes are to be used, rehydration is accomplished by simply adding an aqueous solution, e.g., distilled water, to the liposomes and allowing them to rehydrate.

The liposomes of the present invention may also be remote loaded with ionizable agents according to the disclosure of Bally et al., U.S. application Ser. No. 749,161, filed Jun. 26, 1985, entitled "Encapsulation of Antineoplastic Agents in Liposomes", relevant portions of which are incorporated herein by reference. In this procedure, a transmembrane potential is created across the bilayers of the liposomes during formation, and the ionizable agent is loaded into the liposomes by means of the transmembrane potential. This potential is generated by creating a concentration gradient for one or more charged species (e.g., $Na^+$, $K^+$ and/or $H^+$) across the liposome membranes. The concentration gradient is created by producing liposomes having different internal and external media, i.e., internal and external media having different concentrations of one or more charged species. The liposomes may be dehydrated prior to or following loading with agent.

The present invention decreases the ulcerogenic effect of NSAIDs, and may improve the efficacy of such drugs. In addition, such protection may be afforded by the liposomes of the present invention against ulcers produced by stress or alcohol consumption.

In the ulcer protection embodiment of the present invention, ulcerogenic activity of free indomethacin was compared to that of liposome-entrapped indomethacin.

In the anti-inflammatory bioactivity embodiment of the present invention, efficacy of the liposome-drug preparations was measured by the edema intensity of a paw previously injected with an edema producing amount of carageenan.

Reduction of edema following administration of free NSAID such as indometbacin was compared to that following treatment with liposome-entrapped indomethacin.

MATERIALS AND METHODS

Lipid Purification

Digalactosyl diglyceride (DGDG) was obtained commercially or was prepared from fresh spinach leaves according to the following procedure:

One hundred grams of spinach leaves were chopped into 1 cm pieces and placed in a Waring blender with 300 ml of isopropanol at 70–80° C. the mixture was blended on high speed for two minutes. The resulting slurry was filtered through two layers of Whatman #1 filter paper and the residue washed with 200 ml of the hot isopropanol. The resulting filter cake was placed in the blender with 200 ml chloroform:isopropanol (1:1 v/v) and blended as above. The resulting homogenate was filtered as above and the residue washed with 200 ml of chloroform:isopropanol (1:1 v/v) and then 200 ml chloroform. The filtrate was rotoevaporated in vacuo to a lipid film. The film was then dissolved in 200 ml chloroform, and the solution washed three times with 100 ml of 1% (weight:volume) sodium chloride aqueous solution in a separatory funnel. The organic phase was separated and 5 ml benzene were added to the organic phase. The organic solvent was removed in vacuo to produce a film. The film was resuspended in 10 ml benzene and the separation and solvent removal steps were repeated. The film was stored suspended in 25 ml of chloroform.

The digalactosyl diglyceride was purified from the above film suspension by the following procedure: Fifteen grams of silicic acid that had been activated by baking at 100° C. for three hours was combined with 50 ml of chloroform. The silicic acid slurry was packed into a 20 cm×40 cm column and the bed washed twice with chloroform. 175 g (5 ml) of the lipid solution was loaded onto the column and the flow rate adjusted to 3–5 ml per minute. 175 ml of chloroform was applied to the column, removing pigments in 12 ml fractions; followed by 70 ml of chloroform:acetone (1:1 v/v) applied to the column; followed by 700 ml of acetone. The first (5) 12 ml fractions contain MGDG, followed by DGDG in fractions 9–14, and finally phospholipids, in the remaining fractions which were discarded. Purity of the DGDG was assayed using thin layer chromatography ("TLC"), according to the procedures of Rouser, et al. (Lipid Chromatographic Analysis, Dekker Inc., New York, 1, pp. 99–162, 1967).

Fractions containing DGDG, as determined by TLC were combined and rotoevaporated under reduced pressure to a film. Chloroform (10 ml) was added and the solution transferred to a pre-weighed flask, and rotoevaporated under reduced pressure to a film. The flask containing lipid film was again weighed and the difference calculated to be the weight of the lipid.

The present invention is exemplified by the following Examples, but the scope of the invention is not limited thereto.

EXAMPLE 1

SPLV Procedure—DGDG

Digalactosyl diglyceride (DGDG) (500 mg) (obtained from Serdary Research Laboratories, London, Ontario, Canada) in chloroform at 5 mg/ml was combined with 25 mg of indomethacin in a round bottom flask. The chloroform was removed by evaporation under reduced pressure. Diethyl ether (5 ml) was added to the resulting lipid-drug film and the film resuspended. The flask was placed in a bath sonicator and 1.0 ml of PBS pH 7.4 was added. The solvent was removed under a nitrogen stream while sonicating. The resulting lipid-drug paste was rehydrated with 2.5 ml PBS at pH 7.4. Resulting liposomes contained 10 mg/ml indomethacin.

Control 1

Twenty 225–250 g male Wistar rats were starved for 18–24 hours prior to dosing. Rats were allowed access to water throughout the study. Ten rats in the free drug control group were then administered one oral dose of indomethacin, dissolved in polyethylene glycol 400 at 7 mg/ml and administered at 10 mg/kg body weight of indomethacin.

Four hours following dosing, rats were sacrificed by carbon dioxide anoxia and their stomachs surgically removed by severing at the cardiac and pyloric sphinctors. The stomachs were opened along the lesser curve, flattened, and washed with saline. Ulcer lengths were counted under a dissecting microscope (American Optical, Buffalo, N.Y.) equipped with an eyepiece micrometer, and lengths were summed and averaged for all animals in a single treatment group.

Ulcer protection was assessed by summing and averaging ulcer lengths (in mm) of the treated, group and comparing that value to that of the group administered liposomal drug (Example 3). Percent ulcer inhibition was calculated by dividing the average length of ulceration of the liposome-treated group by that of the corresponding free drug group, and multiplying by 100.

EXAMPLE 2

The procedures and materials of Example 1 were employed using 10 mg/kg body weight of indomethacin entrapped in stable plurilamellar vesicles (SPLVs) composed of digalactosyl diglyceride; ulcer protection was assessed as in Control 1. Table 1 demonstrates that the oral administration of indomethacin in DGDG liposomes ameliorates the ulcerative activity of indomethacin, as compared to that of free indomethacin.

Control 2

Eight female Wistar rats weighing approximately 100 grams were allowed free access to food and water. A tatoo line was inscribed onto the right rear paw just below the hair line. Initial paw volume was measured by a transducer-linked plethysmometer (Stoelting Co., Chicago, Ill.) which contained a saline solution. The instrument measures paw volumes by an electrical charge difference across two electrodes resulting from the volume displacement by the paw. A transducer corrects this charge difference into cubic centimeters of volume displaced. Following immersion of the paw in the perspex cell to the inscribed line, a direct measurement of the displacement volume was recorded.

Rats were orally dosed with 2 mg/kg body weight of indomethacin in polyethylene glycol 400.

At 30 minutes post treatment, rats received an injection of 0.1 ml of 1.5% carageenan in saline (1.0M NaCl) directly into the rear paw pad. The paw volume was again determined 2.5 hours after the carageenan administration. The edema intensity (EI) was calculated:

$$\text{Edema Intensity} = \frac{\text{Final paw volume} - \text{initial paw volume}}{\text{Initial paw volume}}$$

and averaged for the eight rats.

The paw volumes for the eight rats were averaged and the percent swelling inhibition was calculated:

% Swelling Reduction:

$$\frac{\text{Untreated control avg. } EI - \text{Treated group avg. } EI}{\text{Untreated control avg. } EI} \times 100$$

EXAMPLE 3

The procedures and materials of Control 2 were employed using 2 mg/kg of indomethacin entrapped in SPLVs made with DGDG. Rats were orally dosed with the liposomes, and percent swelling reduction was calculated as in Control 2. Table 2 shows the comparable swelling reduction of free indomethacin (Control 2) and DGDG-liposome entrapped indomethacin in this acute carageenan paw edema model.

TABLE 1

| TREATMENT | INDOMETHACIN DOSAGE (mg/kg) | mm ULCERATION | % ULCER INHIBITION |
|---|---|---|---|
| Free Indomethacin in Vehicle | 10 | 43.9 | — |
| Indomethacin-DGDG SPLVs | 10 | 1.1 | 97.5 |

TABLE 2

| TREATMENT | INDOMETHACIN DOSAGE (mg/kg) | % SWELLING REDUCTION |
|---|---|---|
| Free Indomethacin | 2 | 37.2 |
| Indomethacin-DGDG-SPLV | 2 | 36.9 |

What is claimed is:

1. A composition comprising a liposome which comprises:
   (i) a lipid consisting essentially of a glycolipid; and,
   (ii) a non-steroidal anti-inflammatory drug.

2. The composition of claim 1, wherein the liposome is a stable plurilamellar liposome.

3. The composition of claim 1, wherein the glycolipid is a glycosphingolipid or a galactolipid.

4. The composition of claim 3, wherein the glycolipid is a galactolipid.

5. The composition of claim 4, wherein the galactolipid is monogalactosyl diglyceride or digalactosyldiglyceride.

6. The composition of claim 5, wherein the galactolipid is digalactosyl diglyceride.

7. The composition of claim 1, wherein the non-steroidal anti-inflammatory drug is selected from the group consisting of acemetacin, alclofenac, azapropazone, benoxaprofen, benrilate, carprofen, cholinemagnesium trisalicylate, diclofenac, diflunisal, etodolac, fenbufen, fenclofenac, fenoprofen, fentiazac, feprazone, flufenamino acid, fluribiprofen, glucametacin, ibuprofen, indomethacin, indoprofen, isoxicam, ketoprofen, magnesium salicylic acid, meclofenamic acid, mefenamino acid, methylsalicylate, naproxen, niflumic acid, osmosin, oxaprozin, oxyphenbutazone, phenylbutazone, piroxicam, pirprofen, salicylamide, salicylic acid, salicylic acid acetate, salicylsalicylic acid, sodium salicylate, sulindac, suprofen, tenoxicam, tiaprofenic acid, tolmetin and zomepirac.

8. The composition of claim 7, wherein the drug is ibuprofen.

9. The composition of claim 7, wherein the drug is indomethacin.

10. The composition of claim 7, wherein the drug is naproxen.

11. The composition of claim 7, wherein the drug is piroxicam.

12. The composition of claim 7, wherein the drug is salicylic acid acetate.

13. The composition of claim 1, comprising a pharmaceutically acceptable carrier.

14. The composition of claim 13, wherein the carrier is adapted for oral administration.

15. A method of treating a mammal for inflammation, pain or fever comprising administering to the mammal an amount of the composition of claim 13 which comprises a therapeutically effective amount of the nonsteroidal anti-inflammatory drug.

16. A pharmaceutical composition comprising:
(a) a pharmaceutically acceptable carrier; and,
(b) a liposome which comprises:
   (i) a lipid component comprising a glycolipid; and,
   (ii) a non-steroidal anti-inflammatory drug.

* * * * *